United States Patent [19]
Slaby

[11] Patent Number: 5,472,666
[45] Date of Patent: Dec. 5, 1995

[54] PROCESS AND APPARATUS FOR CLEANSING AND/OR DISINFECTION OF ROTATING INSTRUMENTS IN DENTAL CLINICS

[76] Inventor: Jochen Slaby, Zur Rosenau 7, D-65 594, Runkel, Germany

[21] Appl. No.: 281,755

[22] Filed: Jul. 28, 1994

[30] Foreign Application Priority Data

Aug. 11, 1993 [DE] Germany .................... 43 26 956.7

[51] Int. Cl.$^6$ ...................................... A61L 2/18
[52] U.S. Cl. ................. 422/28; 422/300; 422/292; 134/170
[58] Field of Search ............... 422/28, 292, 300; 433/92, 104; 134/152, 166 R, 170

[56] References Cited

U.S. PATENT DOCUMENTS

| | | | |
|---|---|---|---|
| 4,752,444 | 6/1988 | Bowen et al. | 422/28 |
| 5,165,503 | 11/1992 | Hoffman | 433/104 |
| 5,225,160 | 7/1993 | Sanford et al. | 422/28 |
| 5,318,443 | 6/1994 | Overmyer | 433/104 |
| 5,348,711 | 9/1994 | Johnson et al. | 422/292 |

FOREIGN PATENT DOCUMENTS

| | | | |
|---|---|---|---|
| 0321415 | 6/1989 | European Pat. Off. | 422/300 |
| 003900108A | 7/1990 | Germany . | |
| 0297560 | 9/1928 | United Kingdom . | |
| 2248188 | 4/1992 | United Kingdom | 422/28 |

*Primary Examiner*—Robert J. Warden
*Assistant Examiner*—Theresa T. Snider
*Attorney, Agent, or Firm*—W. Thad Adams, III

[57] ABSTRACT

The present invention relates to a process and an appratus for cleansing and/or disinfection of a rotating instrument in a dental clinic wherein the instrument is disposed within a casing provided with at least two openings and is sprayed with cleansing and/or disinfecting agents, wherein the casing is connected via an opening to the vacuum network of the dental clinic and an air current entraining and distributing the injected agent is sucked through the casing. In accordance with a preferred embodiment, portion of the sucked-in air current is used for driving a propeller by which the instrument to be cleaned is set in rotation.

7 Claims, 6 Drawing Sheets

PROCESS AND APPARATUS FOR CLEANSING AND/OR DISINFECTION OF ROTATING INSTRUMENTS IN DENTAL CLINICS

TECHNICAL FIELD AND BACKGROUND OF THE INVENTION

In dental medicine, intensive use is made of rotating instruments by which teeth are treated, using boring, grinding and polishing bodies. In this connection, liquid grinding or polishing pastes are frequently employed which based on the rotation of the instrument have the tendency to penetrate, together with water, saliva and blood, along the shafts of the boring, grinding and polishing bodies into the interior of the rotating instruments.

Similarly, part of these materials creeps back to the boring, grinding or polishing body. In this way, in fact, a permanent exchange of foreign material takes place between the interior of the rotating instruments and the boring, grinding or polishing bodies.

The abrasive properties of the foreign substances penetrating into the instruments promote rapid corrosion of the ball or journal bearings and of the other movable parts so that the life of the precision instruments is considerably reduced. For maintaining a long operation, intensive maintenance of the instruments is therefore indispensable.

Because of the permanent exchange of partly infectious foreign substances between the interior of the instruments and the boring, grinding or polishing bodies makes clear that for hygienic reasons a thorough cleansing and disinfection of the instruments after each patient treatment would be advisable.

The external area of the rotating instruments will be disinfected after each treatment. This is normally done by spraying with suitable disinfecting agents. By so doing, however, a small portion of the agents reaches the instruments. The larger portion is sprayed past the instruments and pollutes the air of the room.

Maintenance of the internal area of the instruments is executed normally only once at the end of a treatment day. This maintenance consists in passing a maintenance liquid through the interior of the instruments. It has been shown that a high cleaning effect is obtained if the movable parts in the instruments are rotated while the maintenance liquid is passed therethrough. A major part of the hitherto-employed maintenance procedures provides that the liquid is introduced into the rotating instruments and is ejected when it is in operation.

It is therefore common to make the rotating instruments run in order to spin away the residues. It cannot be excluded that residual liquid will exit while the patient is being treated.

In a predominant number of treatment cases, the maintenance liquid is applied from spray cans. This has the consequence that in addition to the volatile constituents included in the maintenance liquids, propellant gases are also released into the air of the room. When performing maintenance measures in the interior surfaces of the rotating instruments after each treatment of a patient, which should basically be required, the concentration of harmful substances in the ambient air of the dental treatment room together with further sources of harmful substances would reach a dangerous level.

Starting from the above-described state of the art, it is now the aim of the present invention to provide an extensively self-performing disinfecting and cleansing process for the rotating instruments in dental clinics by which the aforementioned disadvantages are extensively avoided.

SUMMARY OF THE INVENTION

According to the invention, this problem is solved by a process for cleansing and/or disinfection of a rotating instrument used in a dental clinic wherein the instrument is disposed within a casing provided with at least two openings and is sprayed with cleansing and/or disinfecting agents, wherein the process is characterized in that the casing is connected via an opening to the vacuum network of the dental clinic and an air current entraining the injected agent, and distributing the agent through the casing.

The process so designed avoids contamination of the room air by volatile constituents of the cleansing and disinfecting agents and of the propellant gases in connection therewith.

It has shown to be very suitable if, in accordance with the process of the invention, the instrument to be cleansed is rotated during the treatment with the disinfecting and/or cleansing agent, which can be executed by means of an electrically or pneumatically operated motor. It has in this connection shown to be particularly advantageous if portion of the air current sucked through the casing is employed for driving a propeller by which the instrument to be cleansed is set in rotation.

The insertion of the cleansing and/or disinfecting agent in the casing is suitably performed, in accordance with the process of the present invention, by means of a dosing device by which a defined amount is injected from a reservoir into the sucked-in air current.

During sucking-through of the cleansing and/or disinfecting agent, the external side of the rotating instruments is simultaneously sprayed with the agent.

The apparatus for performing the process of the invention is characterized according to the invention by a casing which receives the instrument and comprises an opening to be connected to the vacuum network of the dental clinic and at least one further opening for the entry of the sucked-in air into the casing and an injecting apparatus for spraying the agent into the casing.

In an apparatus so characterized, the injected agent arrives aimedly onto the instrument to be cleansed and neither the volatile constituents included in the cleansing agent nor the common propellant gases have an harmful effect on the room atmosphere.

Furtheron, the cleansing or disinfecting agent, respectively, is suitably disposed in a reservoir integrated within the casing and for the cleansing operation is added to the sucked-in air current in the desired amount by means of a dosing device.

In accordance with a particularly advantageous embodiment of the apparatus according to the invention, the instrument inserted into the casing can be set in rotation by means of a motor driven electrically or by compressed air.

In accordance with a particularly simply designed embodiment, the air current sucked-in through the second opening is passed, at least partly, over a propeller for rotating the instrument to be cleansed.

The air sucked through the casing is suitably passed through a trap prior to leaving the casing, which may for instance consist of a sheet of filter paper.

The reservoir(s) for the cleansing and/or disinfecting liquid may advantageously be disposed on the outside of the apparatus and may be connected via a hose duct(s) to the apparatus according to the invention. Such embodiment is particularly suitable in case of a solidly installed apparatus since larger reservoirs can be used so that refill is less often required.

When the cleansing, maintenance and disinfecting process according to the invention has been finished, the instrument so treated can unlimitedly be used, based on a drying phase integrated in the process.

Since for the transportation of the cleansing and/or disinfecting liquid the sucking-off system is already available in the dental clinic, the use of spray cans is not necessary. The ecologic benefit is apparent; the economic benefit results from the fact that costly packaging materials and the employment of propellants is avoided. The volatile constituents are removed through the suction system and the liquid constituents are eliminated in the siphon provided thereafter. There is no pollution of the room atmosphere.

BRIEF DESCRIPTION OF THE DRAWINGS

In the following, the invention will be explained in more detail, based on exemplified embodiments shown in the attached drawings, wherein.

DESCRIPTION OF THE PREFERRED EMBODIMENT AND BEST MODE

Figure 1:
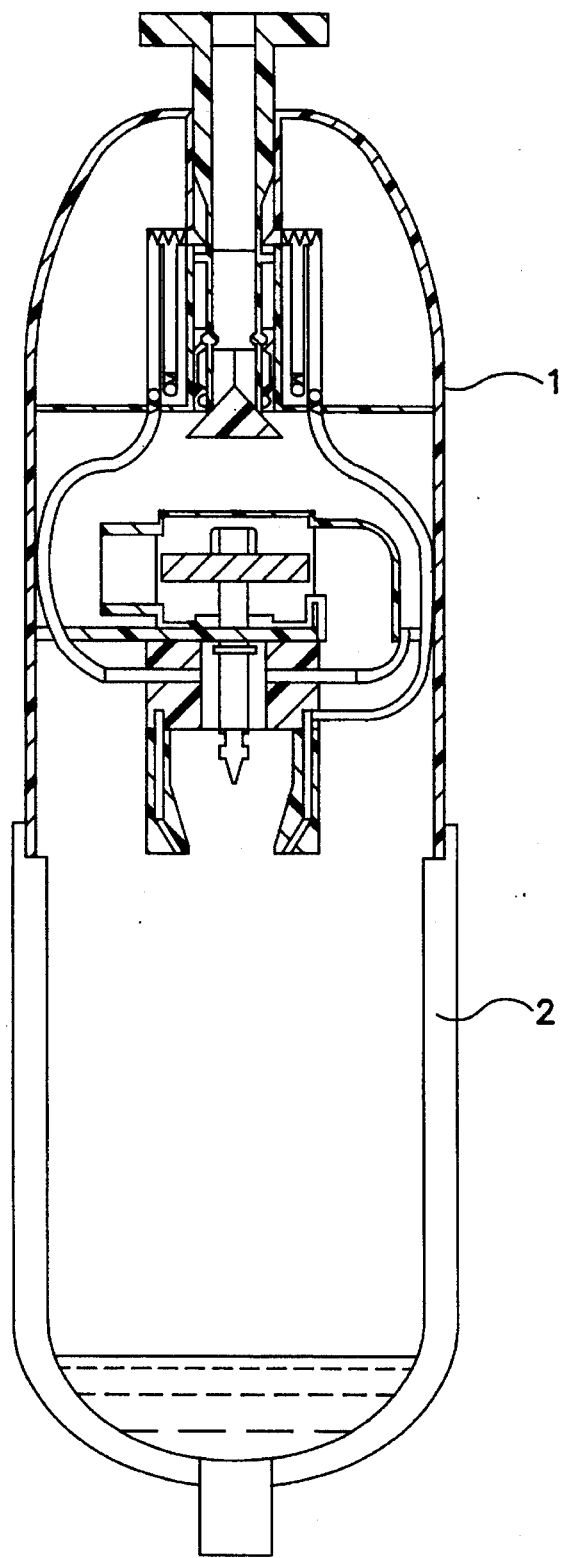
FIG. 1 is a sectional view of the apparatus according to the invention.

As shown in FIG. 1, the apparatus according to the invention comprises a multiple-portion, preferably two-portion casing 1 and 2. The arrangement of the casing portions may be either vertical or horizontal, the vertical arrangement being preferred. As can be taken from FIG. 2, the upper casing portion 1 comprises a base plate 3 through which a drive shaft 4 is provided. On the upper side of base plate 3, a propeller 5 is secured to drive shaft 4. At the end of drive shaft 4 opposite to propeller 5, a driver 6 is provided. Propeller 5 is surrounded by a housing 7 open on two sides serving the steering of the air current. One side is connected with a passage opening 8 through base plate 3. A different version of the invention provides that there is no housing 7 and that the air current is steered solely by the arrangement of passage openings 8 and 20.

On the side of base plate 3 averted from propeller 5, drive shaft 4 is surrounded by a bushing 9. Within the bushing 9, a channel 10 is provided which is connected with a passage 11 through base plate 3, on one side, and is open towards drive shaft 4 on the other. A further channel 12 is connected to a valve 13 which is connected with a liquid reservoir 14. This channel 12 is also open towards drive shaft 4. The liquid reservoir 14 is preferably disposed within the apparatus shown (FIG. 1), whereby it is immaterial in which area of the apparatus it is arranged. The preferred version of the invention also provides that two, or a plurality, of liquid reservoirs 14, 15 are provided which are disposed in the upper area of casing portion 1. A different version provides that also liquid reservoirs are used which are disposed outside of the apparatus.

On the side of bushing 9 averted from base plate 3, a holding fixture 16 is provided the shape of which can be adapted to the rotating instrument to be treated. In the lower portion of bushing 9, a channel 17 is axially provided the end of which is connected to the valve 18 of a further liquid reservoir 15. From axially arranged channel 17, one, or a plurality of, exit passages 19 are going out directed to the center. The axially arranged channel 17 including exit passages 19 may also be provided outside bushing 9 and holding fixture 16.

A passage opening 20 extends through casing portion 1 which can be locked by a lock 22 secured to draw bushing 21. The outer diameter of draw bushing 21 is so designed that when it is operated, stems 23, 24 for dosing valves 25, 26 can be moved. At the end of draw bushing 21 provided outside the casing, there is a button 27 which makes movement of draw bushing 21 possible. Button 27 is air-penetrable.

Figure 2:
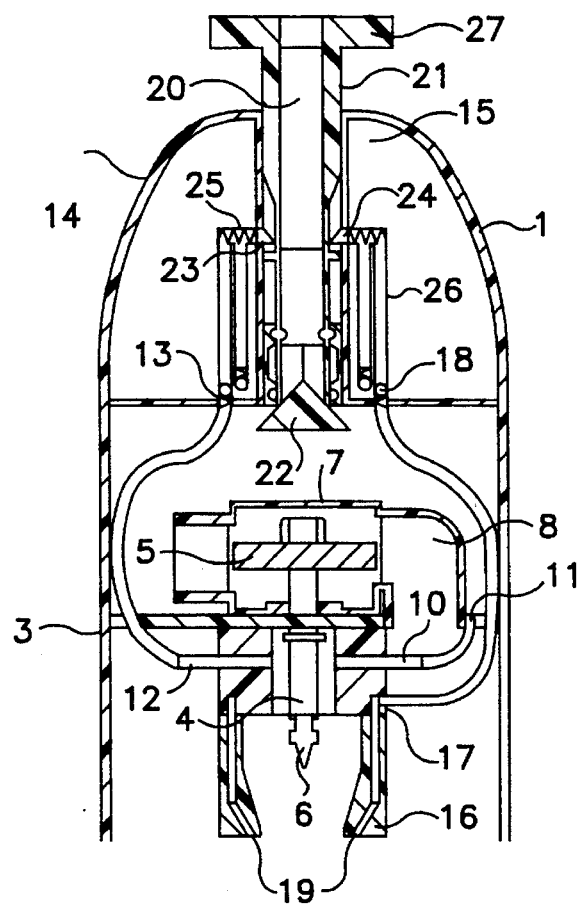
FIG. 2 is a portional view (upper casing portion) of the apparatus of the invention in cross section.
Figure 3:
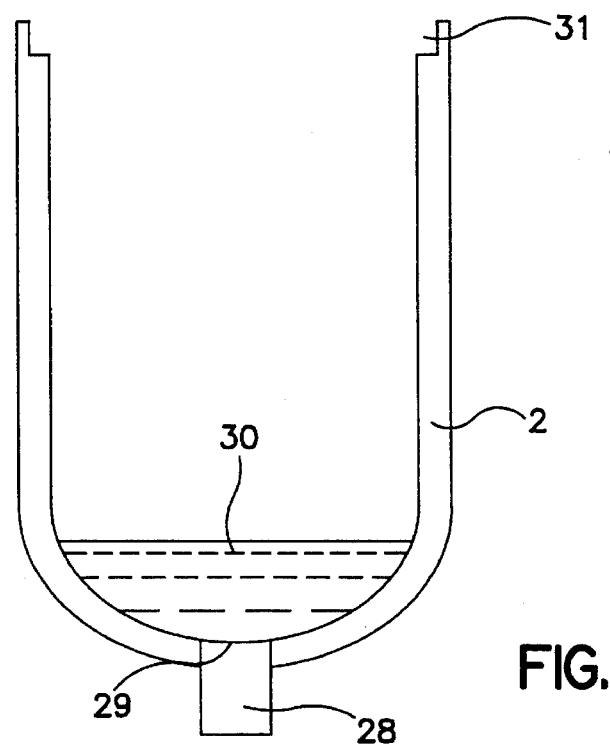
FIG. 3 is a portional view (lower casing portion) of the apparatus of the invention in cross section.

In the lower casing portion 2 shown in FIG. 2, the counter part to casing portion 1, there is provided, at one end thereof, a connecting socket 28 by which the apparatus can be connected, either if necessary or permanently, to the draining system normally available in dental clinics. In front of the exit opening 29 from casing portion 2, a liquid siphon system 30 is provided. For this purpose, a filter is for instance suitable which should be exchanged at regular intervals. The casing wall 31 opposite connecting socket 28 is so shaped that casing portion 1 can tightly be fixed to it.

The operation described in the following of the apparatus according to the invention refers to an embodiment having a vertically arranged two-part casing 1, 2, two integrated liquid reservoirs 14, 15 and a propeller 5 disposed in a housing, the propeller being driven by the suction current. In front of the exit opening 29 within the apparatus, a cellulose filter 30 binding the used liquid is provided.

The supply of the cleansing, maintening and/or disinfecting liquids can be performed manually, mechanically or by means of pneumatically or electrically operated valves.

Figure 4:
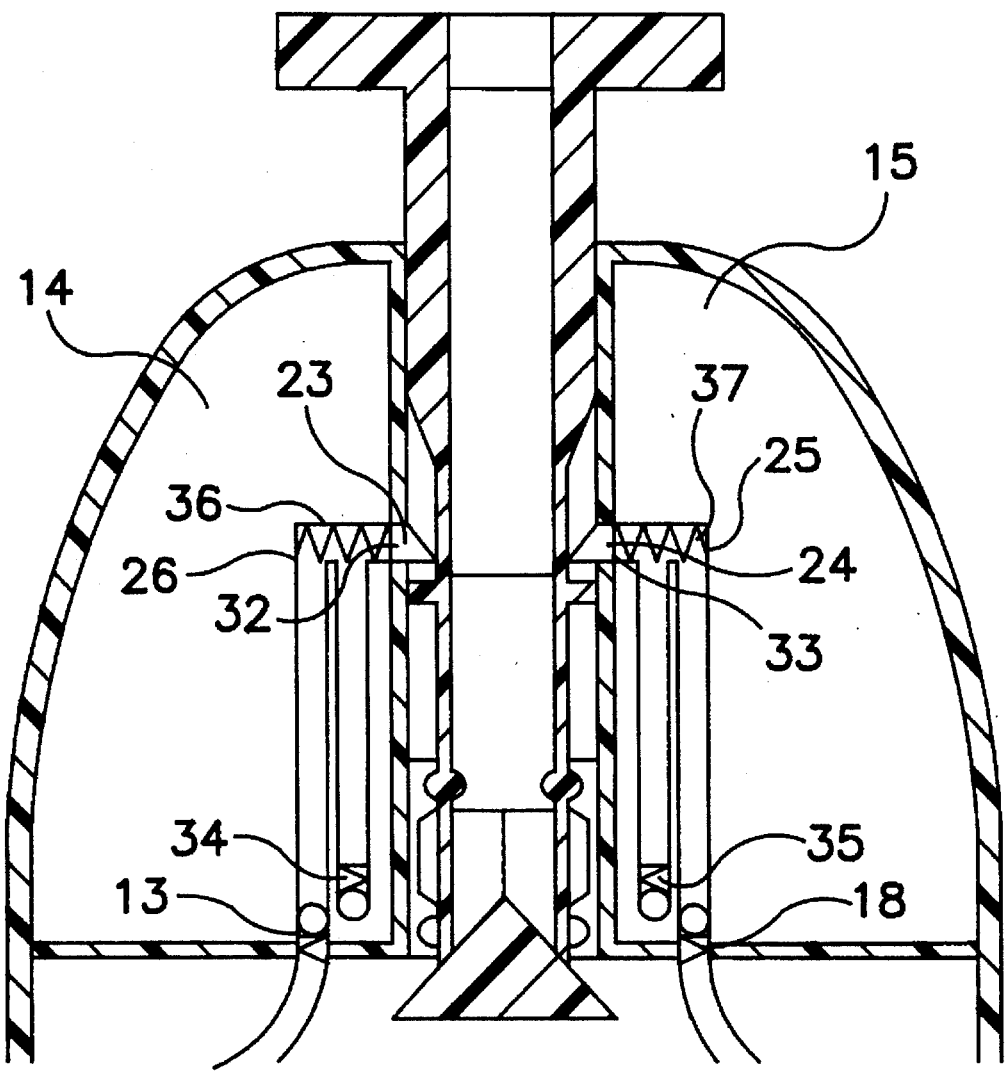
FIG. 4 is a portional view (dosing device) of the apparatus of the invention in cross section.

In the operation described, the injection of the agent into the rotating instrument or the spraying of the outer area is executed by emptying hollow bodies 25, 26 (see FIG. 4) which are additionally provided in reservoirs 14, 15. For this purpose, exit openings including ball valves 13, 18 are provided at the lower end of reservoirs 14, 15. Within the hollow bodies provided in reservoirs 14, 15, a piston each 32, 33 which can be moved in forward and backward direction and two openings each are provided. One opening each is connected to the ball valve in exit opening 13 and 18, respectively, the other one with a ball valve 34 and 35, respectively, in the reservoir, which permits the inflow of liquid into the hollow bodies but closes in case of pressure in the hollow bodies. Pistons 32, 33 in hollow bodies 25, 26 are kept by spring pressure 36, 37 to one end of the hollow body. As soon as pistons 32, 33 are moved against the spring pressure which happens by stem 23, 24 when pressing down draw bushing 21, pressure is generated in the hollow bodies 25, 26 and the liquids are ejected. The spring pressure in the hollow bodies 25, 26 leads to a reset of pistons 32, 33 as soon as draw bushing 21 is drawn up thus causing liquid to be sucked through ball valves 35 into hollow bodies 25, 26.

Figure 5:
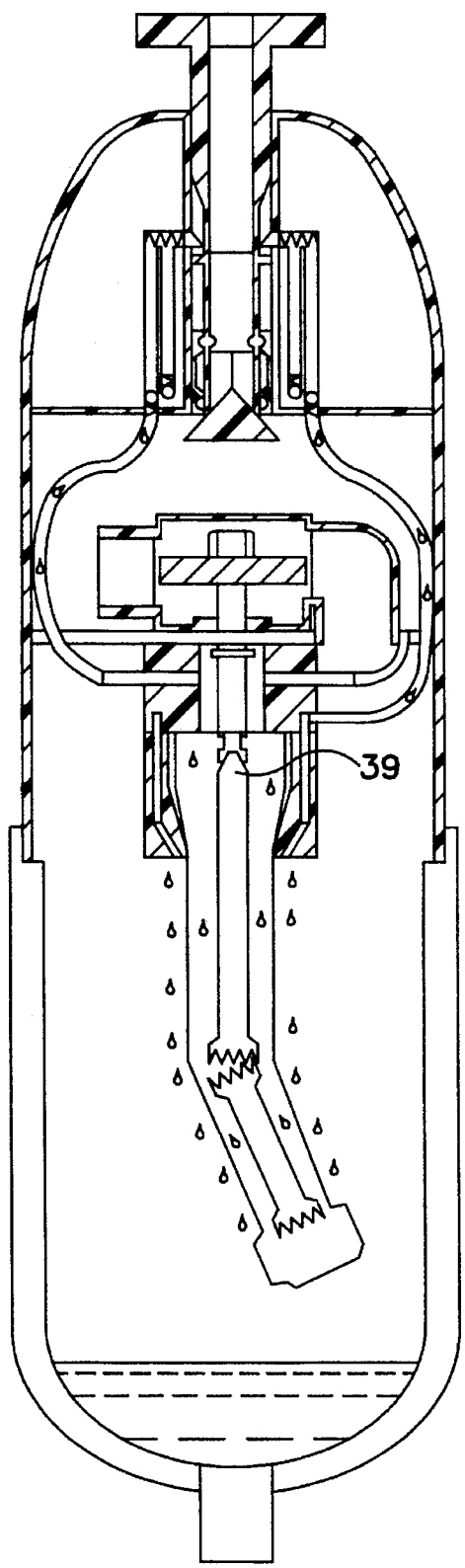
FIG. 5 is a cross sectional view of the apparatus of the invention when performing the cleansing operation with the instrument to be cleansed inserted.

Before starting a cleansing and disinfecting process, casing portion 1 is removed from casing portion Subsequently, a rotating instrument 38 is inserted into holding fixture 16 until it is fixed. In this case, the upper edge of the instrument rests against the lower face of bushing 9. Unless anyway solidly installed, casing portion 2 including connecting socket 28 is inserted into the suction channel receiver provided in the selective depot at the open end of the suction tube. Subsequently, casing portion 1 is put onto casing portion 2. As shown in FIG. 5, there is a connection between drive shaft 4 and the drive mechanism 39 of the rotating instrument 38.

Figure 6:
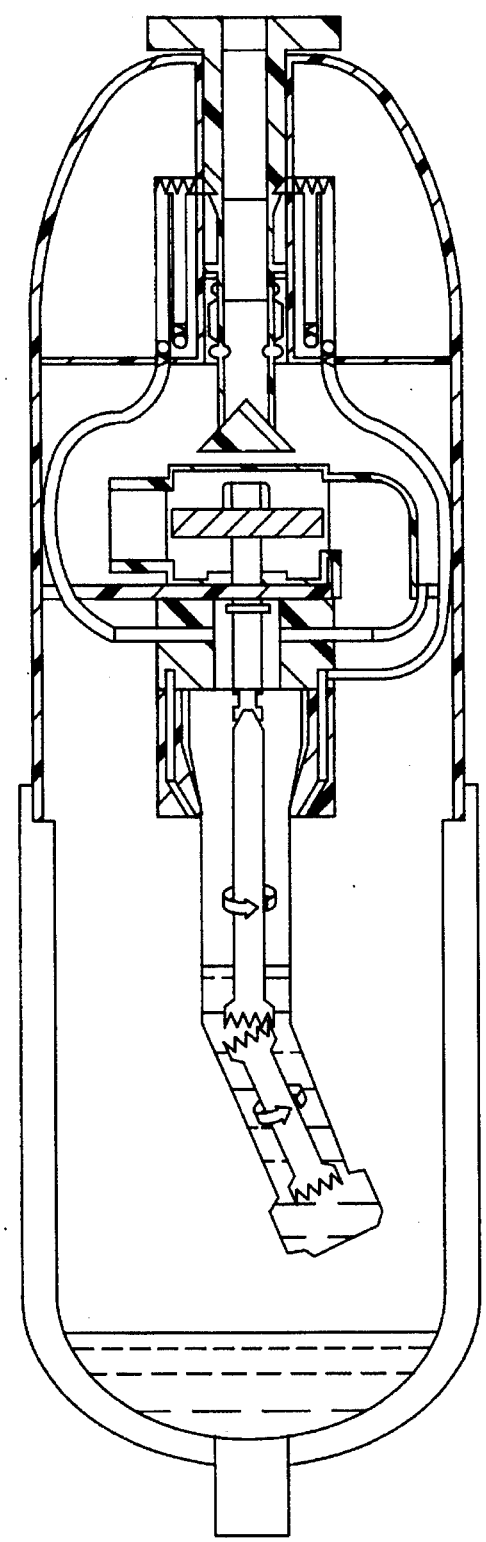
FIG. 6 is a cross sectional view of the apparatus of the invention.
Figure 7:
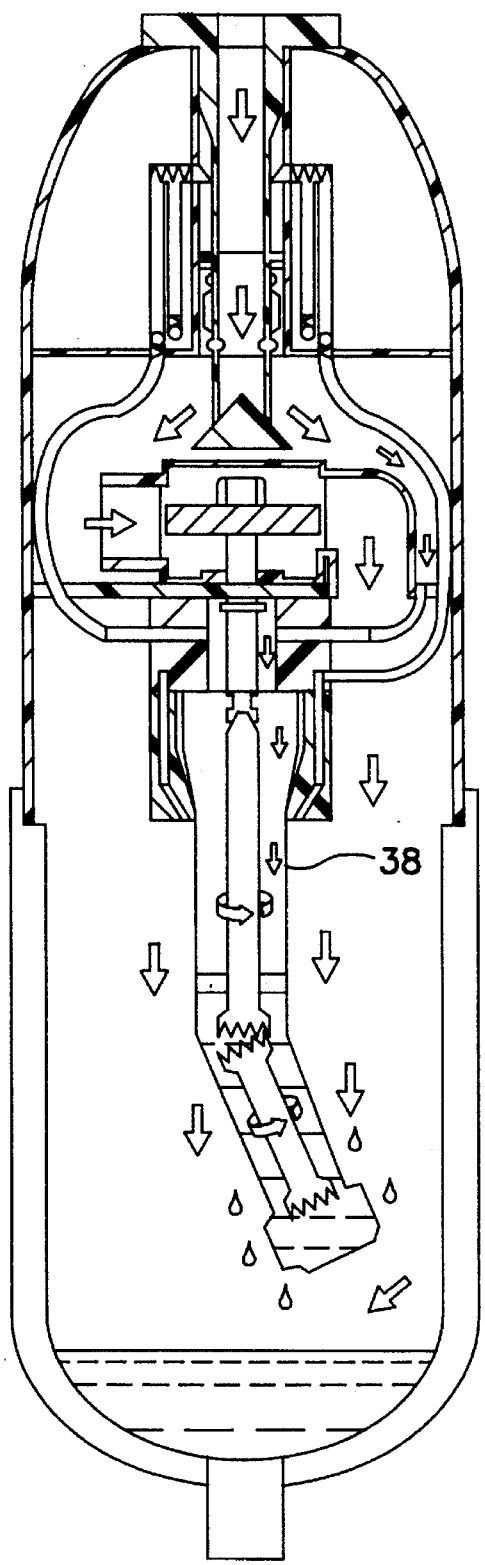
FIG. 7 is a cross sectional view of the apparatus of the invention showing the flow of the air current.

When pressing down draw bushing 21, pistons 32, 33 are pressed by stems 23, 24 into hollow bodies 25, 26. This causes firstly that the liquid from reservoir 14 is injected into the interior of rotating instrument 38. At the same time, the outer face is sprayed with disinfectant from reservoir 15 through axially passing channel 17 and exit passage 19. At this stage, lock 22 opens passage opening 20 (see FIG. 6). By starting the suction machine, or by connecting the suction hose, air is sucked off by the apparatus of the invention. This air is passed over propeller 5 which subsequently starts to rotate drive shaft 4. The driving forces are transferred via driver 6 to drive shaft 4 of the drive mechanism of rotating instrument 38. The instrument starts to rotate. Part of the air is passed via passage 11 through the interior of the instrument. By this, the maintaining liquid is sucked through the instrument. The disinfecting liquid is transported by the external air current (see FIG. 7). When the liquid has been sucked through the instrument, the latter is passed by air only. Excessive liquid is removed from the instrument.

There remains only a protective film on the movable parts of the instrument. The volatile constituents of the liquid are drained together with the suction current while the liquid constituents are absorbed by filter 30. As soon as the suction motor is switched off, or the suction hose is removed from casing portion 2, respectively, casing portion 1 is again separated from casing portion 2. Draw bushing 21 is drawn upwardly and the cleansed, disinfected rotating instrument 38 ready for use is taken from the apparatus.

I claim:

1. A process for cleansing and/or disinfection of a rotating instrument used in a dental clinic, comprising the steps of:
   (a) disposing the instrument within a casing provided with at least two openings, said casing being connected via one of said at least two openings to a vacuum network of the dental clinic;
   (b) spraying the instrument with cleansing and/or disinfecting agents by sucking, via the vacuum network, an air current entraining the agents into said casing, thereby distributing the agents through said casing; and
   (c) rotating the instrument being cleaned and/or disinfected by means of a propeller located within said casing, the propeller being driven by a portion of the air current.

2. A process according to claim 1, and comprising the step injecting the cleansing and/or disinfecting agent into the sucked-in air current by means of a dosing device.

3. A process according to claim 1, and comprising the step of spraying an outside of the instrument with said cleansing and/or disinfecting agent during sucking-through of said cleansing and/or disinfecting agent.

4. An apparatus for cleansing and/or disinfection of a rotating instrument used in a dental clinic, comprising:
   (a) a casing for holding the instrument to be cleansed and/or disinfected, said casing including a vacuum connecting opening for being connected to a vacuum network of the dental clinic, and at least one entrance opening for receiving a cleansing and/or disinfecting agent into said casing, the cleansing and/or disinfecting agent being entrained in a sucked-in air current generated by the vacuum network;
   (b) an injecting apparatus for spraying the cleansing and/or disinfecting agent into the casing; and
   (c) rotation means located within said casing for rotating said instrument during cleansing and/or disinfection.

5. An apparatus according to claim 4, wherein the injecting apparatus comprises a dosing device located within said casing for spraying a predefined amount of said cleansing and/or disinfecting solution into the sucked-in air current.

6. An apparatus according to claim 4, and including a least one reservoir formed within said casing and proximate the injecting apparatus for holding said cleansing and/or disinfecting solution.

7. An apparatus according to claim 4, wherein the rotation means comprises a propeller located within said casing and operatively connected to the instrument to be cleansed and/or disinfected, said propeller being driven by the sucked-in air current for rotating the instrument.

* * * * *